US009694400B2

(12) United States Patent
Kautzman et al.

(10) Patent No.: US 9,694,400 B2
(45) Date of Patent: Jul. 4, 2017

(54) CONTROLLED VERIFIED REMEDIATION OF EXCAVATED SPOIL

(71) Applicants: Keith Kautzman, Mandan, ND (US); Bruce Goines, Yukon, OK (US)

(72) Inventors: Keith Kautzman, Mandan, ND (US); Bruce Goines, Yukon, OK (US)

(73) Assignee: Wildfire Construction LLC, Dickinson, ND (US)

( * ) Notice: Subject to any disclaimer, the term of this patent is extended or adjusted under 35 U.S.C. 154(b) by 27 days.

(21) Appl. No.: 14/751,888

(22) Filed: Jun. 26, 2015

(65) Prior Publication Data

US 2016/0375471 A1    Dec. 29, 2016

(51) Int. Cl.
| | | |
|---|---|---|
| *B09C 1/00* | (2006.01) | |
| *B09C 1/08* | (2006.01) | |
| *B09C 1/02* | (2006.01) | |
| *G01N 33/24* | (2006.01) | |
| *B09C 1/06* | (2006.01) | |

(52) U.S. Cl.
CPC ............... *B09C 1/02* (2013.01); *B09C 1/065* (2013.01); *B09C 1/08* (2013.01); *G01N 33/24* (2013.01)

(58) Field of Classification Search
CPC .................................... B09C 1/00; B09C 1/08
USPC ..... 405/128.1, 128.7, 128.75, 128.8, 128.85, 405/128.9
See application file for complete search history.

(56) References Cited

U.S. PATENT DOCUMENTS

| | | |
|---|---|---|
| 4,810,280 A | 3/1989 | Le Van Mao et al. |
| 5,082,488 A | 1/1992 | Van Mao |
| 5,234,498 A | 8/1993 | Graves, Jr. |
| 5,387,738 A | 2/1995 | Beckham et al. |
| 5,484,533 A | 1/1996 | Crawford et al. |
| 5,690,833 A | 11/1997 | Crawford et al. |
| 5,711,383 A | 1/1998 | Terry |
| 6,039,128 A | 3/2000 | Brunato |
| 6,702,044 B2 | 3/2004 | Reddy et al. |
| 7,137,448 B2 | 11/2006 | Di Lullo Arias et al. |
| 7,140,439 B2 | 11/2006 | Luke et al. |
| 7,147,067 B2 | 12/2006 | Getzlaf |
| 7,150,321 B2 | 12/2006 | Luke et al. |
| 7,156,174 B2 | 1/2007 | Roddy et al. |
| 7,297,664 B2 | 11/2007 | Santra et al. |
| 7,544,640 B2 | 6/2009 | Luke et al. |
| 8,227,381 B2 | 7/2012 | Rodrigues et al. |
| 8,356,678 B2 | 1/2013 | Perez-Cordova |
| 2005/0072599 A1 | 4/2005 | Luke et al. |
| 2006/0247484 A1* | 11/2006 | Matthews ............. B09B 3/0025 588/249 |
| 2007/0015948 A1 | 1/2007 | Cadieux et al. |
| 2009/0062594 A1 | 3/2009 | Cadieux et al. |

(Continued)

FOREIGN PATENT DOCUMENTS

JP    2010269275    * 12/2010

OTHER PUBLICATIONS

Machine Translation of JP2010269275, Sep. 18, 2016, 13 pages.*

*Primary Examiner* — Sunil Singh
(74) *Attorney, Agent, or Firm* — Keaty Law Firm LLC

(57) ABSTRACT

A system and method for controlled verified remediation of excavated contaminated spoil using a sorbent in a verified process of testing and analysis of spoil before and after remediation and of adjusting amounts of sorbent and supplemental water mixed with contaminated spoil.

16 Claims, 7 Drawing Sheets

(56) References Cited

U.S. PATENT DOCUMENTS

2014/0349894 A1    11/2014    Quintero et al.
2014/0371113 A1    12/2014    Fout et al.

* cited by examiner

CONTROLLED VERIFIED REMEDIATION OF EXCAVATED SPOIL

BACKGROUND OF THE INVENTION

This invention provides a system and method for remediation of excavated contaminated spoil, using a sorbent in a verified process of testing and analysis of spoil before and after remediation and of adjusting amounts of sorbent and supplemental water mixed with contaminated spoil.

Digging into the Earth—mining, drilling, excavating, and dredging—is a method of obtaining materials and energy and of shaping the built environment. Such digging produces spoil, or removed earth, rock, and sludge, in the form of cuttings, tailings, gangue, overburden, interburden, and waste. Such spoil might be contaminated with toxins and carcinogens such as radioactive materials, heavy metals, hydrocarbons, and other deleterious substances harmful to terrestrial and aquatic plant and animal life either directly or indirectly. If such contaminated spoil is not properly remediated, then the contaminates are likely to migrate out of the spoil and into the environment, as either airborne particles or aterborne suspensions or solutions.

The handling of spoil by digging and drilling operators is highly regulated, and improper handling of spoil is subject to fines and penalties.

Construction aggregate is coarse particulate material such as sand, gravel, crushed stone, slag, recycled concrete, and geosynthetic aggregates used in construction as a reinforcing component and a low-cost extending component of composite materials such as concrete, and as a stable, water-conductive foundation, base, or bed material for roads, drains, buildings, and other construction.

Organic wastes can be destroyed by incineration at high temperatures; however, if the waste contains heavy metals or radioactive isotopes, these must be separated and stored, as they cannot be destroyed. The method of storage will seek to immobilize the toxic components of the waste.

Contaminated spoil is often generated in remote mining, drilling, excavating, and dredging sites. If remediation of such contaminated spoil is to be performed in an off-site facility, then the heavy, bulky, contaminated spoil must be transported in its contaminated state to the off-site facility, which is an expensive and potentially dangerous operation. On-site remediation techniques have the advantage of not requiring transport of contaminated spoil, but existing on-site techniques have the disadvantages of a much greater chance of techniques being performed incorrectly in the field by on-site personnel using on-site equipment, as opposed to personnel and equipment in an off-site, central remediation facility, and on-site techniques and operations are often insufficiently documented to provide verifiable data for review by in-house environmental-quality managers and governmental regulators.

There exists a need for a system and method providing controlled verified remediation of excavated contaminated spoil which can be set up on-site at remote locations, which analyzes each batch of contaminated spoil and analyzes the remediating agent, which applies the proper amount of remediating agent and the proper amount of additional water according to the analysis of the contaminated soil and the remediating agent, and which analyses and verifies the resulting remediated aggregate.

Various patents discuss the use of zeolite as a cementitious substance for encapsulating drill cuttings and the use of zeolite in wash water as a surfactant, as a catalyst, etc.

U.S. Pat. No. 5,711,383 issued on Jan. 27, 1998 to Dralen T. Terry et al. for "Cementitious Well Drilling Fluids and Methods" discloses an invention that provides cementitious well drilling fluids and methods of drilling subterranean well bores. The drilling fluids are basically comprised of water, a water viscosity increasing material and a cementitious material which when deposited on the walls of the well bore as a part of the filter cake thereon consolidates the filter cake into a stable mass that readily bonds to a cementitious material slurry subsequently placed in the well bore. The methods of drilling a subterranean well bore are basically comprised of the steps of preparing a drilling fluid of the invention and drilling a subterranean well bore using the drilling fluid. The consolidated filter cake layers have the physical properties required to prevent pressurized fluid migration in the annulus after the annulus is cemented. A variety of cementitious materials can be utilized in the drilling fluid in accordance with this invention. For example, the cementitious material may be any of the various hydraulic cements which are commonly utilized, both normal particle size and fine particle size. Examples of some of such cements are blast furnace slag, Portland cement and mixtures thereof. Another cementitious material which can be utilized is comprised of a silicious containing substance combined with an activator such as hydraulic cement, lime or an alkali. Suitable silicious containing substances include silicates, amorphous silica, e.g., fumed silica and colloidal silica, rice hull ash, zeolites and volcanic glass.

U.S. Pat. No. 6,039,128 issued on Mar. 21, 2000 to Siro Brunato for "Method and System for Obtaining Core Samples During the Well-Drilling Phase by Making Use of a Coring Fluid" discloses a method and system for obtaining core samples using a coring fluid. During the drilling phase of hydrocarbon wells and the like, drilled with existing drilling systems, the bit that drills the well is driven by a string of rotating pipes and drilling mud is introduced in the rotating pipes. The drilling mud rises carrying with it the cuttings produced by the drill bit. Alternatively, the rotating pipes can be removed and a special piece of equipment called a core barrel is mounted thereon. The rotating pipes thus equipped for collection of the "core" are then lowered into the well. When the rotating pipes are at the bottom of the hole, a sufficient volume of a colloidal, viscous coring or embedding fluid is introduced into the mud circuit to encapsulate a sample of the cuttings, for lifting to the surface and subsequent analysis. The fluid prevents the cuttings from being altered by the drilling mud. In order to obtain core samples of underground formations, drilling and mud circulation in the bore are momentarily suspended, while a certain volume of coring matrix. fluid, that is to say a fluid with an adhesive effect that serves to encapsulate the cuttings, is introduced into the mud circuit at surface. Normal mud circulation is then resumed, pushing the matrix fluid to the well bottom, after which drilling is resumed, so that the matrix fluid passing through the. nozzles in the drill bit hits the cuttings in their virgin state as they are formed and incorporates them a gelatinous mass, protecting them from direct contact with the mud and thus avoiding the washing effect. The cuttings thus coated by the matrix fluid and pushed upward by the mud circulation reach the surface and are collected and analyzed.

U.S. Pat. No. 6,702,044 issued on Mar. 9, 2004 to B. Raghava Reddy et al. for "Methods of Consolidating Formations or Forming Chemical Casing or Both While Drilling" discloses methods of consolidating formations or forming chemical casing or both while drilling. One method of the invention comprises drilling a well bore with a drilling fluid comprised of water, a polymeric cationic catalyst which is absorbed on weak zones or formations formed of unconsolidated clays, shale, sand stone and the like, a water soluble or dispersible polymer which is cross-linked by a thermoset resin and causes the resin to be hard and tough when cured, a particulate curable solid thermoset resin, a water soluble thermoset resin, and a delayed dispersible acid catalyst for curing the solid and water soluble resins. The drilling fluid forms a filter cake on the walls of the well bore that cures and consolidates the unconsolidated weak zones and formations penetrated by the well bore so that sloughing is prevented and forms a hard and tough cross-linked chemical casing on the walls of the well bore. According to the method, one or more insoluble chemical casing reinforcing materials are selected from the group consisting of carbon fibers, glass fibers, mineral fibers, cellulose fibers, silica, zeolite, alumina, calcium sulfate hemihydrate, acrylic latexes, polyol-polyesters and polyvinyl butyral.

U.S. Pat. No. 7,147,067 issued on Dec. 12, 2006 to Donald A. Getzlaf for "Zeolite-Containing Drilling Fluids" discloses methods and compositions for wellbore treating fluids, especially drilling fluids that comprise zeolite and a carrier fluid. In this patent, zeolite is used as a suspending agent in a drilling fluid, whereby the drilling fluid has sufficient carrying capacity and thixotropy to transport cuttings through the annulus and out to the surface. The zeolite acts as a suspending agent for one or more of cuttings, a weighting agent, and loss circulation material. Portions of a zeolite-containing drilling fluid are left on the walls of a wellbore as part of a filter cake, and/or in permeable areas affecting the wellbore, such as fissures, fractures, caverns, vugs, thief zones, low pressure subterranean zones or high pressure subterranean zones. According to such an embodiment, the zeolite in the portions of the drilling fluid left in the wellbore acts as a settable material, which can be caused to set by an activator. According to one embodiment, a subsequent composition that contains at least one activator is pumped into the wellbore to come into contact with the drilling fluid left therein. In one such embodiment, the subsequent composition containing at least one activator is a treating fluid, such as a mud, pill, or spotting fluid, and is pumped into the wellbore prior to primary cementing operations. According to another embodiment, the subsequent composition containing at least one activator is a cement slurry pumped into the wellbore during cementing operations. When the activator in the subsequent composition contacts the drilling fluid in the filter cake and/or permeable areas, the activator causes the zeolite in the drilling fluid to set. In addition, when the subsequent composition is a cement slurry, as the cement slurry sets, the activator therein diffuses into the drilling fluid left in the filter cake and/or permeable areas in the wellbore. The activator is present in the subsequent composition in a compressive strength developing amount, and may be one or more of calcium hydroxide, calcium oxide, calcium nitrate, sodium silicate, sodium fluoride, sodium silicofluoride, magnesium silicofluoride, zinc silicofluoride, sodium carbonate, potassium carbonate, sodium hydroxide, potassium hydroxide, sodium sulfate, or mixtures thereof. Selection of the type and amount of an activator(s) largely depends on the type and make-up of the composition in which the activator is contained, and it is within the means of those of ordinary skill in the art to select a suitable type and amount of activator.

U.S. Pat. No. 8,227,381 issued on Jul. 24, 2012 to Klin A. Rodrigues for "Low Molecular Weight Graft Copolymers for Scale Control" discloses a low molecular weight graft copolymer comprising a synthetic component formed from at least one or more olefinically unsaturated carboxylic acid monomers or salts thereof, and a natural component formed from a hydroxyl-containing natural moiety. The number average molecular weight of the graft copolymer is about 100,000 or less, and the weight percent of the natural component in the graft copolymer is about 50 wt % or greater based on total weight of the graft copolymer. Processes for preparing such graft copolymers are also disclosed. A variety of adjunct ingredients can be used in the cleaning formulations described in this patent. Useful adjunct ingredients include, but are not limited to, aesthetic agents, anti-filming agents, antiredeposition agents, antispotting agents, beads, binders, bleach activators, bleach catalysts, bleach stabilizing systems, bleaching agents, brighteners, buffering agents, builders, carriers, chelants, clay, color speckles, control release agents, corrosion inhibitors, dishcare agents, disinfectant, dispersant agents, draining promoting agents, drying agents, dyes, dye transfer inhibiting agents, enzymes, enzyme stabilizing systems, fillers, free radical inhibitors, fungicides, germicides, hydrotropes, opacifiers, perfumes, pH adjusting agents, pigments, processing aids, silicates, soil release agents, suds suppressors, surfactants, stabilizers, thickeners, zeolite, and mixtures thereof.

U.S. Pat. No. 8,356,678 issued on Jan. 22, 2013 to Ramon Perez-Cordova for "Oil Recovery Method and Apparatus" discloses a method and apparatus for recovering oil from oil-containing sorbents, such as drill cuttings obtained from drilling with an oil-based mud. The method includes peptizing the substrate with an acid reagent and direct thermal desorption with combustion effluent gases at high temperature under turbulent mixing conditions. Another method disclosed includes upgrading the oil in the substrate to improve one or more of the properties of the recovered oil relative to the oil in the substrate, such as lower aromatics content, lower sulfur content, lower functional group content, higher saturates, higher viscosity, higher viscosity index, and any combination thereof. The apparatus provides for efficient recovery of oil from the substrate with a short residence time, high through-put, low residual oil content in the treated solids and/or high percentage of oil recovery. The apparatus may be transported to a remote location for on-site treatment of drill cuttings or other oil-containing solids. In one embodiment, the oil-based drilling cutting or other substrate may act as a catalyst or as a support for catalysts, e.g., the peptization with acid may expose or form catalytically active surfaces in the sorbent material. In a further embodiment, the oil-based drilling cuttings or other substrate may be amended by the addition of a catalyst such as one or more of zeolites, aluminates, silicates, aluminum silicates, noble metals, etc., added in the peptization step or in the thermal desorber.

U.S. application Publication Number 2014/0349894 published on Nov. 27, 2014 to Lirio Quintero et al. for "Nanofluids and Methods of Use for Drilling and Completion Fluids" discloses nanomaterial compositions that are useful for applications in drilling and completion fluids as enhancers of electrical and thermal conductivity, emulsion stabilizers, well bore strength improvers, drag reduction agents, wettability changers, corrosion coating compositions and the like. These nanomaterials may be dispersed in the liquid phase in low volumetric fraction, particularly as compared to corresponding agents of larger size. Nanofluids (fluids containing nano-sized particles) may be used to drill at least part of the wellbore. Nano fluids for drilling and completion applications may be designed including nanoparticles such as carbon nanotubes. These fluids containing nanomaterials, such as carbon nanotubes, meet the required rheological and filtration properties for application in challenging HPHT drilling and completions operations. Nanoparticles expected to be useful components of completion fluids include nano-silica, nano-alumina, nano-zinc oxide, nano-boron, nano-iron oxide, zeolites carbonates, piezoelectric crystals, pyroelectric crystals and combinations thereof. Other new potential nanoparticles useful as lost circulation additives include, but are not necessarily limited to, nanoparticles physically or chemically bonded to porous or non-porous microparticles (particle size greater than 100 nm), which may impart some properties of the nanoparticles onto the microparticles. Functional groups on nano-sized particles expected to be useful to prevent lost circulation include-nano-silica, nano-alumina, nano-zinc oxide, nano-boron, nano-iron oxide, zeolites carbonates, piezoelectric crystals, pyroelectric crystals and combinations thereof.

U.S. application Publication Number 2014/0371113 published on Dec. 18, 2014 to Gary Fout et al. for "Drilling Fluid Processing" discloses a method of processing a return oil based drilling fluid which includes centrifuging a primarily fluids phase at a first speed and separating the primarily fluids phase into a first effluent and a first residual, centrifuging the first effluent at a second speed and separating the first effluent into a second effluent and a second residual, and centrifuging the second effluent at a third speed and separating the second effluent into a third effluent and a third residual. A surfactant, a polymer, combinations of surfactant(s) and polymer(s) and/or a wash water may be added to one or more of the return oil-based drilling fluid, the primarily fluids phase, the primarily solids phase, the first effluent, the second effluent, and the third effluent. The method of processing a return oil-based drilling fluid includes the steps of dividing the return oil-based drilling fluid into a primarily fluids phase and a primarily solids phase; centrifuging the primarily fluids phase at a first speed and separating the primarily fluids phase into a first effluent and a first residual; centrifuging the first effluent at a second speed, the second speed higher than the first speed, and separating the first effluent into a second effluent and a second residual; and centrifuging the second effluent at a third speed, the third speed higher than the second speed, and separating the second effluent into a third effluent and a third residual. In another aspect, embodiments disclosed in the application relate to a method of processing a return oil-based drilling fluid including adding a volume of a base oil fluid to the return oil-based drilling fluid, wherein the ratio of the volume of base oil fluid added to a volume of the return oil-based drilling fluid is between about 0.1 and 0.4; mixing the base oil fluid with the return oil-based drilling fluid to form a diluted return oil-based drilling fluid; adding a surfactant to the diluted return oil-based drilling fluid; and adding a polymer to the diluted return oil-based drilling fluid. In another aspect, embodiments disclosed in this application relate to method of processing a return oil-based drilling fluid including adding a base oil fluid to a primarily solids phase of the return oil-based drilling fluid, wherein a ratio of a volume of the base oil fluid added to a volume of the primarily solids phase is between 0.1 and 0.2; separating the primarily solids phase into diluted separated fluids and separated solids; adding a wash water to the separated solids; and removing treated solids from the wash water. Chemical additives that may be used in the wash water include surfactants; sodium silicate, zeolites, and other additives useful in the treatment of drilling waste. In some embodiments, the wash water may include biosurfactants which may include oil-digesting microbes. Such microbes digest organic contaminates on surfaces and in soils and convert hydrocarbons, oils, and greases into non-toxic compounds.

SUMMARY OF THE INVENTION

This invention provides a system and method for remediation of excavated contaminated spoil, using a sorbent in a verified process of testing and analysis of spoil before and after remediation and of adjusting amounts of sorbent and supplemental water mixed with contaminated spoil.

The system and method of the present invention solves several existing problems of performing and verifying remediation, especially on-site in remote mining, drilling, and excavating locations.

BRIEF DESCRIPTION OF DRAWINGS

Reference will now be made to the drawings, wherein like parts are designated by like numerals, and wherein.

DETAILED DESCRIPTION OF THE INVENTION

Figure 1:
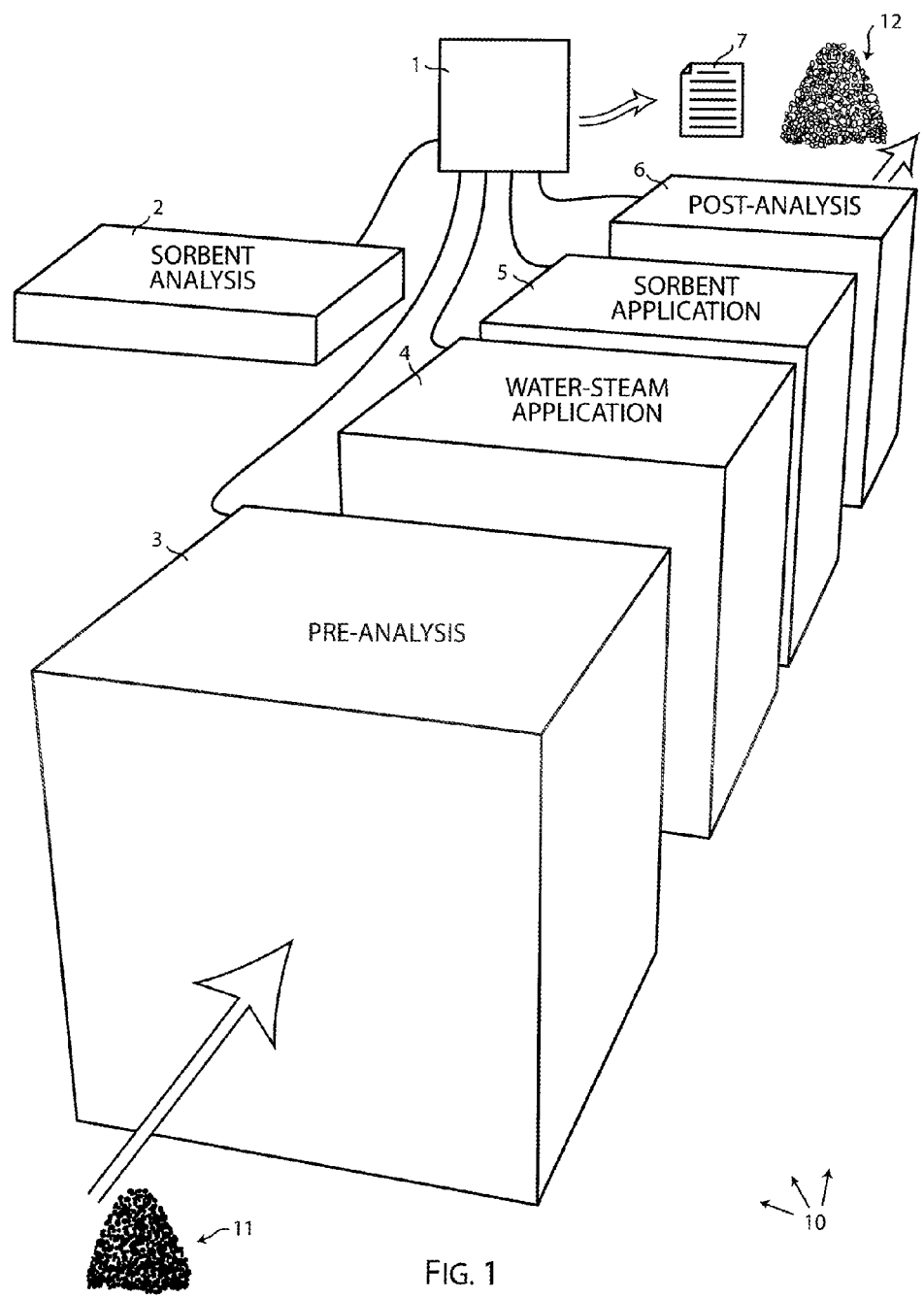
FIG. 1 is a schematic of the steps of the invention.

Referring to FIG. 1, the invention provides a system and method 10 for controlled verified remediation of contaminated spoil 11, yielding remediated aggregate 12. The remediating agent used is a sorbent capable of adsorbing contaminants, such as a zeolite or silica gel or other sorbents known in the art.

Sorbents are effective remediating agents because they act as molecular sieves with crystalline structures trapping, neutralizing, or encapsulating contaminates. Sorbents having a molecular sieve size of 4 Angstroms, such as zeolites and silica gel, are often used because of their high selectivity for molecules with critical diameters less than 4 Å such as $NH_3$, $H_2S$, $SO_2$, $CO_2$, $C_2H_5OH$, $C_2H_6$, and $C_2H_4$, for cationic species such as $NH_4^+$, $Pb^{2+}$, $Cu^{2+}$, $Zn^{2+}$, and $Cd^{2+}$, and for heavy metal ions.

Most such sorbents neutralize or encapsulate contaminants in an exothermic or heat-producing reaction. The heat produced tends to drive such reactions faster and further, sometimes to a point of thermal runaway. Therefore the machinery used to implement this invention should be capable of accommodating very high heat. This produced heat also performs a thermolysis or pyrolysis on the spoil-sorbent mixture, further breaking down or denaturing contaminants. The produced heat often creates a hard ceramic encapsulation or network of encapsulations, which is desirable where radioactivity is present or where some level of contaminates remains in the remediated aggregate, because encapsulation prevents waterborne or airborne leaching or release of contaminates.

Figure 4:
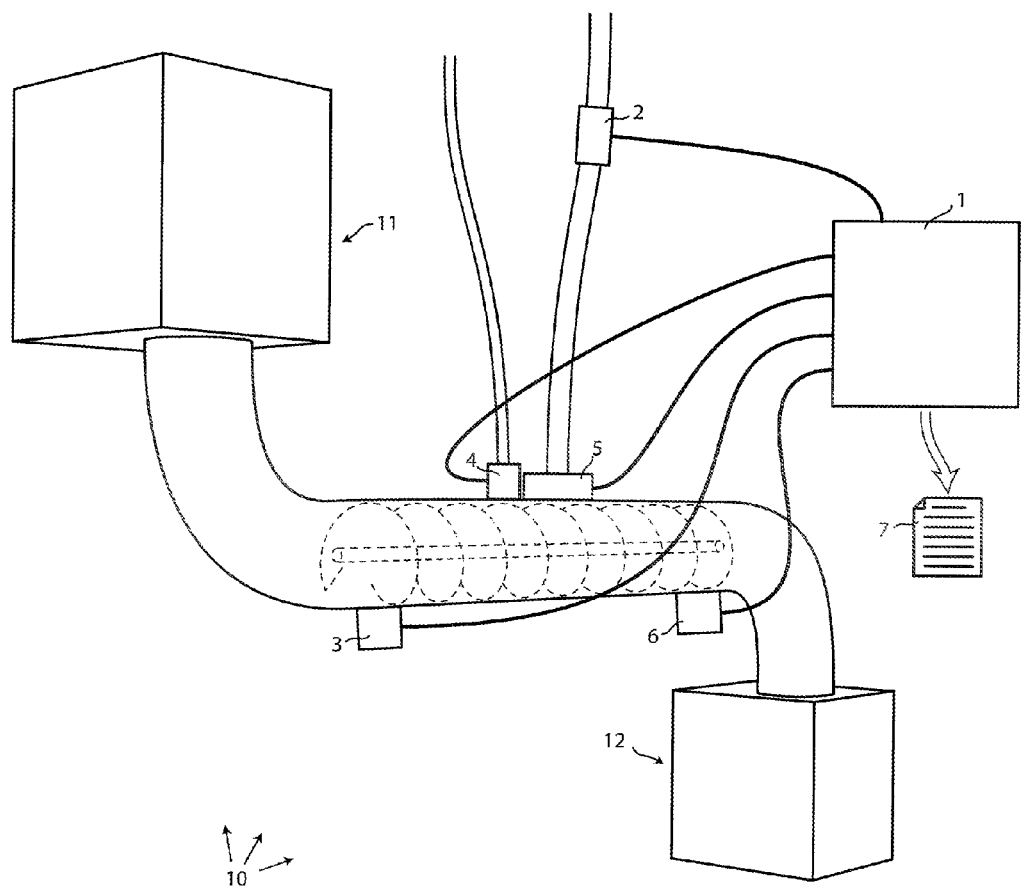
FIG. 4 is a schematic of an automated embodiment of the invention in use.
Figure 6:
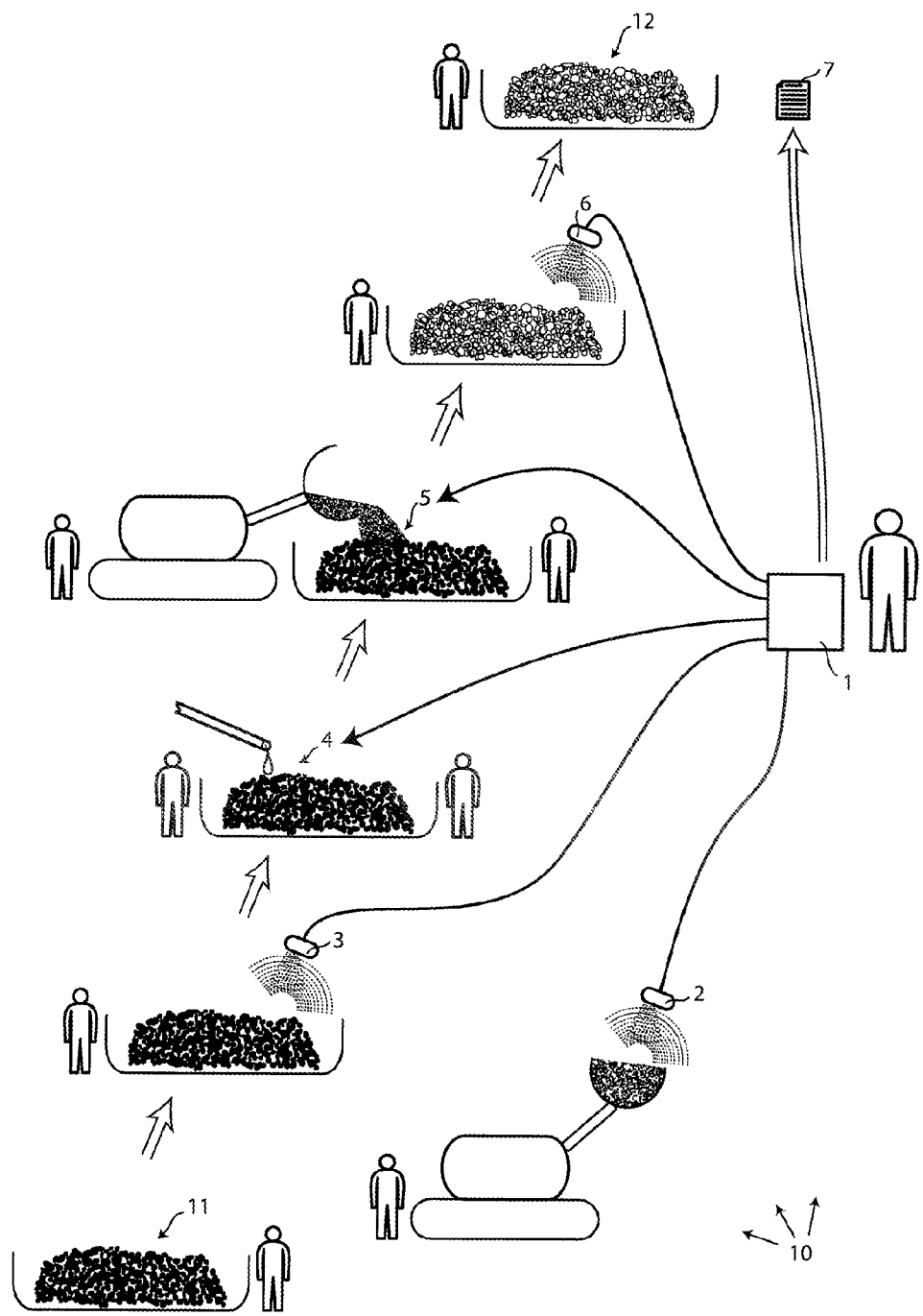
FIG. 6 is a schematic of a large-scale, partly manual embodiment of the invention in use.
Figure 7:
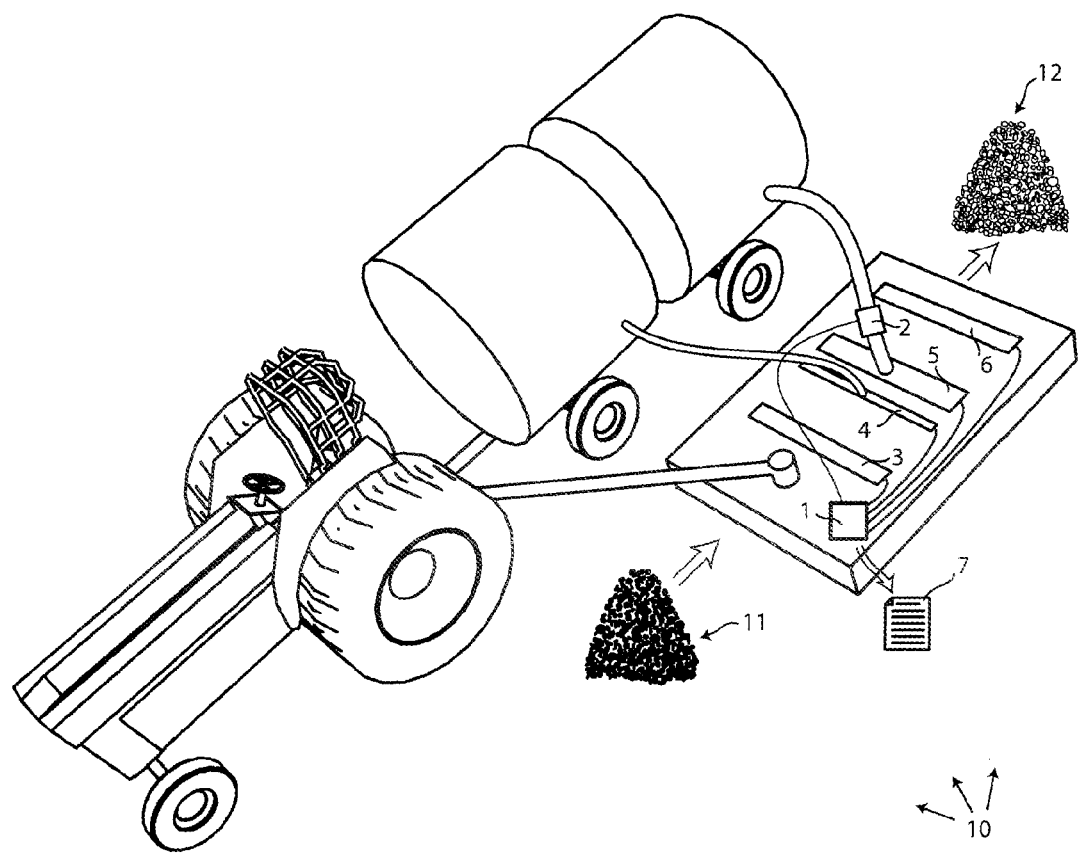
FIG. 7 is a schematic of an embodiment of the invention adapted for mobility in use.

The invention provides a remediation pathway conveying contaminated spoil 11 from an intake point to an output point where it emerges as remediated aggregate 12. The pathway can move the contaminated spoil along a physical path of conveyance, with consecutive steps performed in different adjacent locations, or the pathway can leave the contaminated spoil in one place, with consecutive steps performed in a single location. Many of the steps can be performed either entirely automatically or with manual participation directed by determinations based on analysis of characteristics and conditions according to the method of the invention. Different embodiments of the invention are disclosed here. FIG. 4 shows an automated, contained auger-conveyer system. FIG. 6 shows a large-scale single-location system with manual participation and the use of heavy equipment. FIG. 7 shows a tractor-mounted system designed to be pulled through contaminated spoil.

Returning to FIG. 1, the remediation operation is controlled and is verified by a controller 1 which receives data from, and controls the operations of the components of the system, and derives, records, and reports verification data for the outgoing remediated aggregate.

The controller 1 receives data from sensor groups analyzing the characteristics and conditions of 1) the sorbent before use, 2) the incoming contaminated spoil, and 3) the outgoing remediated aggregate. The sensors contained in such sensor groups are known and available, and include contact sensors, ultrasound sensors, infrared sensors, piezoelectric sensors, ionizing sensors, sniffing sensors, and sensors reading a variety of wavelengths and frequencies.

The sorbent analyzer 2 comprises sensors to analyze the sorbent before the sorbent is used for remediation. Among the characteristics and conditions sensed are the moisture level and the temperature of the sorbent, as well as sorbent-specific characteristics which provide indications of the remediating potency of any specific batch or supply of sorbent.

The pre-analyzer 3 comprises sensors to analyze the contaminated spoil entering the remediation pathway. Among the characteristics and conditions sensed are the moisture level and the temperature of the spoil, as well as characteristics such as the level of heavy metals, hydrocarbons, radioactivity, and other contaminants present or absent in the incoming spoil.

The post-analyzer 6 comprises sensors to analyze the remediated aggregate just prior to exiting the remediation pathway. Among the characteristics and conditions sensed are the moisture level and the temperature of the aggregate, as well as confirmation of the absence of heavy metals, hydrocarbons, or other such contaminates, and, especially if radioactivity is present, confirmation of the desired formation of hard ceramic encapsulations.

The water adder 4 adds water when needed to the incoming contaminated spoil under the control of the controller 1. For most sorbents, and when most sorbents are working on a solid or semi-solid substrate, the presence of water is needed as a solvent to transport contaminates into the molecular sieve structure of the sorbent. Too little moisture content is likely to lessen the effectiveness of the sorbent upon the contaminated spoil because of insufficient water to carry the contaminates into the sorbent. On the other hand, too much moisture, especially if the water is already in the supply of sorbent before it is used, is likely to lessen the effectiveness of the sorbent upon the contaminated spoil because a significant portion of each sorbent particle will be occupied by pure water, and will not accept any more water bearing contaminates. Through the controller 1, using data provided by the sorbent analyzer 2 and the pre-analyzer 3, a determination is made whether added water is needed and the amount, if any, to be added in order to provide an optimum moisture level for reaction with the sorbent.

The water can be added as a stream, a spray, or a mist. The water can optionally be heated, although added heat is only likely to have any significant effect in very cold environments or for sorbents generating a low heat of reaction. The water can optionally be in the form of steam, where steam may be beneficial in penetrating particularly resistant or solid-frozen spoil.

The sorbent adder 5 adds sorbent to the contaminated spoil in the remediation pathway for the purpose of mixing with and reacting with the contaminated spoil at an optimal moisture level. Through the controller 1, using data provided by the sorbent analyzer 2 and the pre-analyzer 3, the optimum amount of the specific supply of sorbent at its specific moisture level, temperature, and other relevant characteristics and conditions, is determined in relation to the relevant characteristics and conditions of the contaminated spoil, and the optimal amount of sorbent is added to the remediation pathway.

After reaction of the sorbent with the contaminated spoil, the resulting remediated aggregate is analyzed by the post-analyzer 6, in order to verify that the remediation was effective and that the resulting remediated aggregate 12 is safe to be used as intended.

Relevant data about each batch or run of the system is recorded by the controller 1, and is available as a set of remediation verification data 7 useful for supervisory and regulatory control and reporting.

Figure 2:
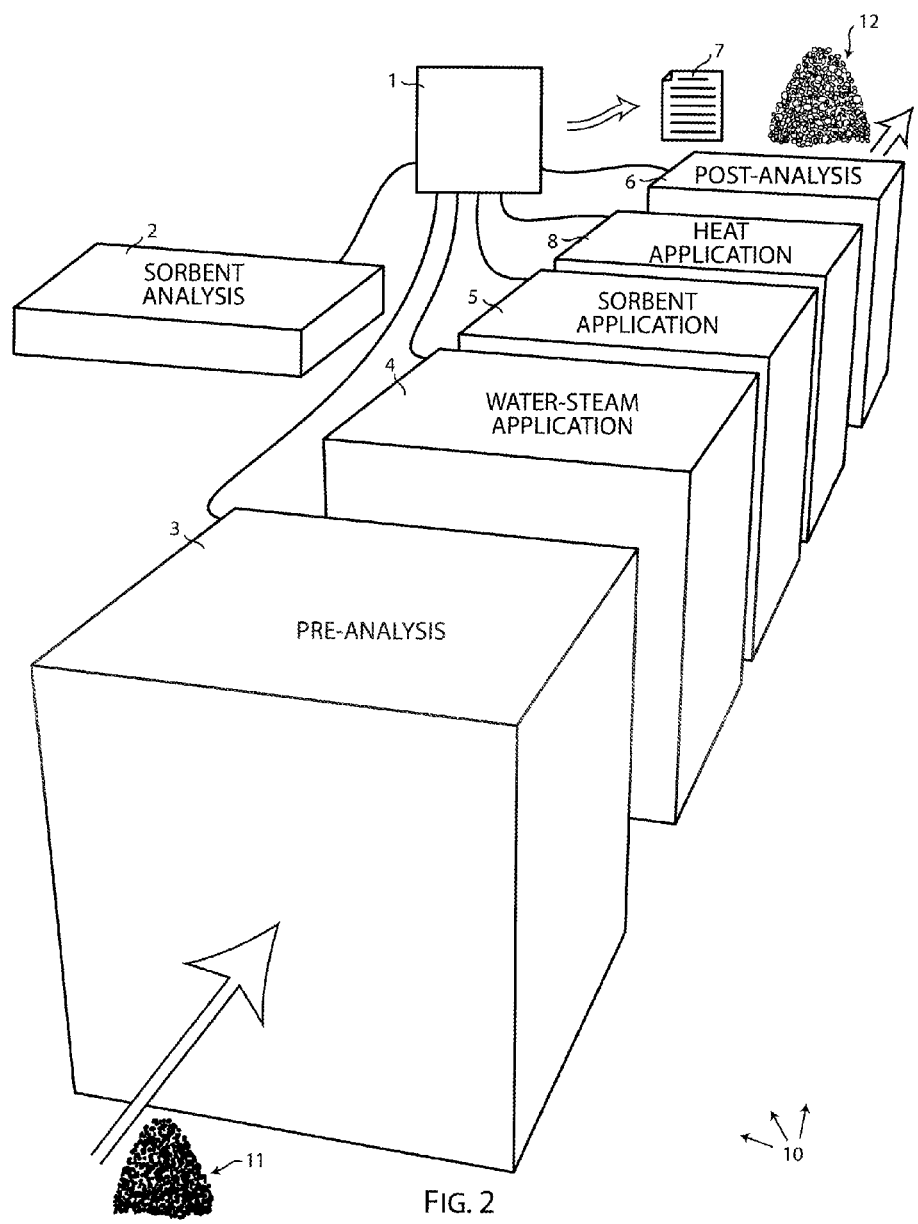
FIG. 2 is a schematic of the steps of the invention having addition of supplemental heat.

Referring to FIG. 2, the invention can optionally have a heat adder 8 in order to ensure that thermolysis and pyrolysis reactions are run to completion and that hard ceramic encapsulations are fully formed. This added heat would be of benefit in extremely cold conditions, extremely dry conditions where remediation is performed at less than optimum moisture levels, and where either the supplied sorbent, the contaminated spoil, or the combination of both generate insufficient heat from the reaction itself.

Figure 3:
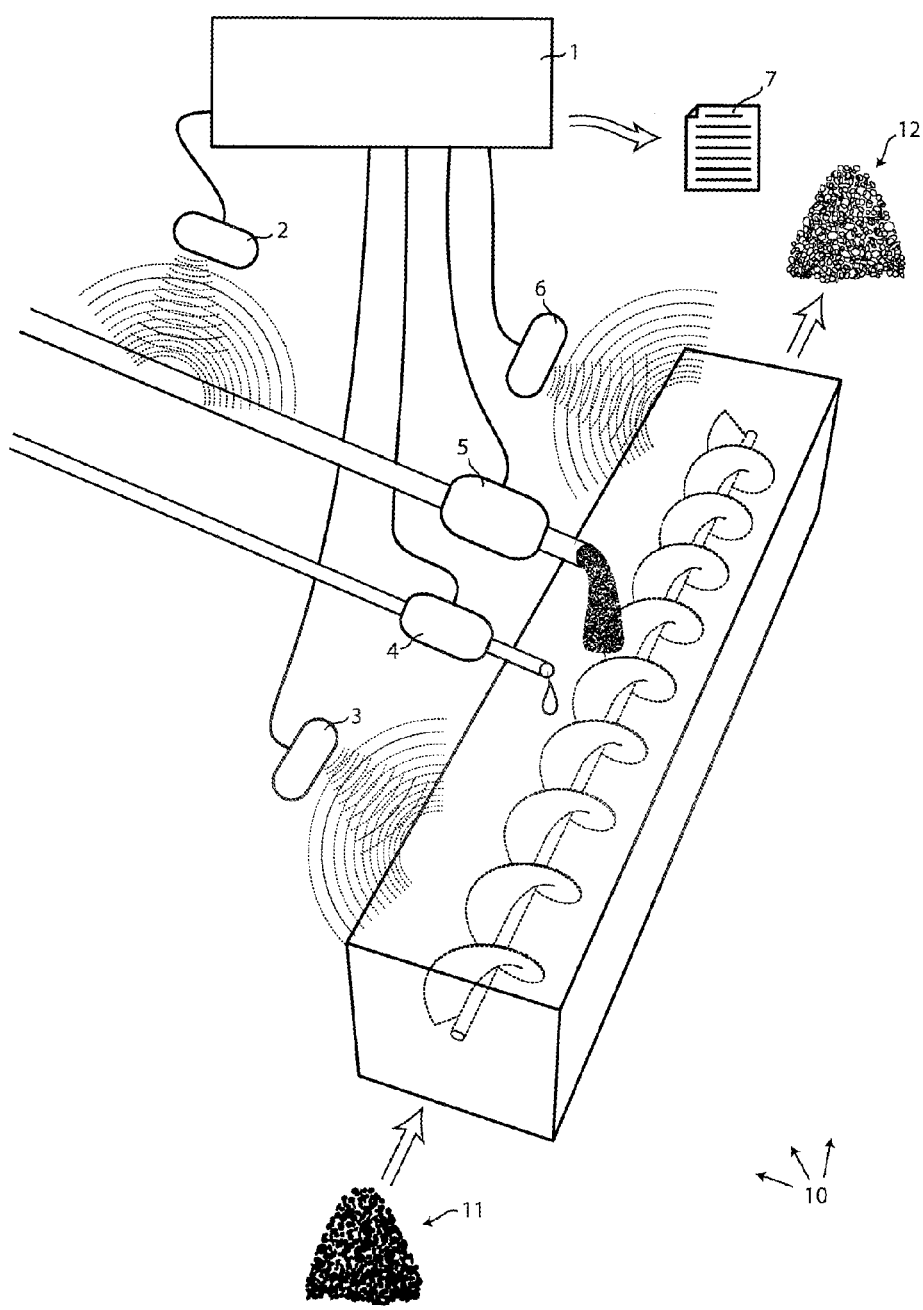
FIG. 3 is a schematic of the invention in use.

Referring to FIG. 3, the system and method of the invention are represented as an automated system moving along the remediation pathway by means of an auger, which is a means of both conveying and mixing the materials.

In use, the system and method for controlled verified remediation of contaminated spoil 10 takes in contaminated spoil 11 at the intake point of the remediation pathway. The spoil is tested and analyzed by the sensor group of the pre-analyzer 3 to determine what contaminates are present, what degree or intensity of remediation is needed, and whether radioactivity is present, because radioactive particles are not neutralized, but instead are encapsulated to prevent their entry into the environment's air or water supply. At approximately the same time, the supplied sorbent is tested and analyzed before use by the sensor group of the sorbent analyzer 2 to determine the potential and potency of the sorbent in terms of such factors as moisture level, temperature, particle size, and other relevant chemical and physical properties.

Data from the sorbent analyzer 2 and the pre-analyzer 3 is sent to the controller 1, and is operated upon with simultaneous reference to both sets of data in order to forecast and determine, among other things, what the combined moisture level of the spoil-sorbent mixture would be in the absence of the addition of more water, whether the remediation reaction would benefit from the addition of more water, and the amount of additional water required to reach an optimum moisture level, and what amount of sorbent should be applied to the contaminated spoil at the optimum moisture level in light of the interactions among the characteristics and conditions of the supplied sorbent and of the contaminated spoil.

Where the controller 1 determines that an amount of water should be added to the contaminated spoil in the remediation pathway in order to achieve an optimum moisture level the controller instructs the water adder 4 to add such an amount of water, which is drawn from a water supply.

The controller 1 then instructs the sorbent adder 5 to add to the contaminated spoil in the remediation pathway the amount of sorbent determined to be proper in light of the analyzed characteristics and conditions.

The resulting spoil-sorbent mixture will undergo the desired adsorption, thermolyis or pyrolysis, and encapsulating reactions or processes, in an exothermic or heat-producing process that will most likely drive the remediation to completion. Optionally, additional heat can be supplied either by heating the added water or by a heat adder 8 as disclosed above.

After the contaminated spoil has been transformed into remediated aggregate by the remediating reactions and processes, the remediated aggregate is tested and analyzed by the sensor group of the pre-analyzer 3 to verify the absence of heavy metals, hydrocarbons, or other such contaminates, and, especially if radioactivity is present, verify the formation of hard ceramic encapsulations.

The remediated aggregate 12 is then discharged at the output point of the remediation pathway. In large-scale, high-throughput operations a marker or tag identifying specific batches or runs can be generated and attached to the remediated aggregate. At approximately the same time, the controller 1 generates a set of remediation verification data derived by and recorded by the controller, specific to and identifying the just-completed batch or run. The remediation verification data provides information about the spoil both before and after the remediation process, about the type and amount of sorbent used, and about the moisture levels, temperatures, and times of the remediation reactions and processes.

Referring to FIG. 4, an embodiment of the invention comprises an automated, contained, auger-driven system capable of essentially continuous automated remediation.

Figure 5:
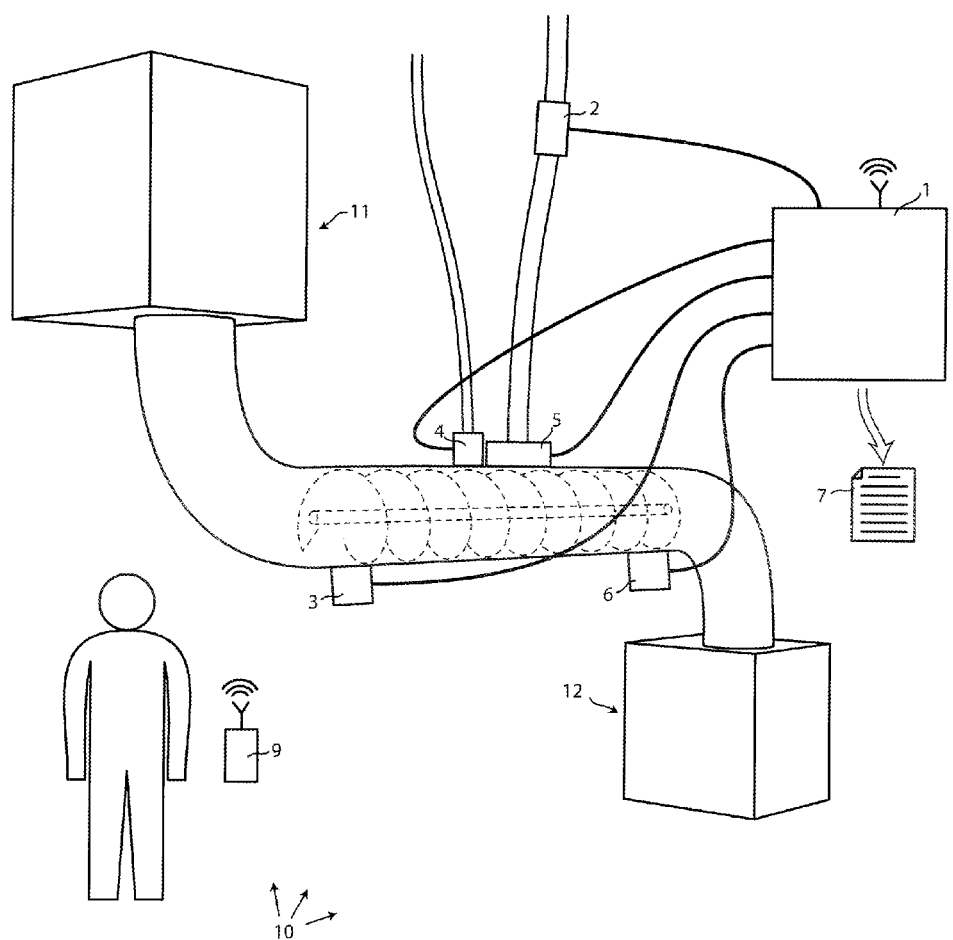
FIG. 5 is a schematic of an automated embodiment of the invention having a remote control in use.

Referring to FIG. 5, an optional addition to an automated embodiment of the invention is a remote controller 9 through which an operator can monitor and control the system.

Referring to FIG. 6, another embodiment of the invention comprises manually performed or partially manually performed steps on a very large batch of contaminated spoil 11 which stays in a single location, with the analyzers 2, 3, 6 and adders 4, 5 being sequentially applied in a mediation pathway, all under the direction of the controller 1.

Referring to FIG. 7, another embodiment of the invention comprises a mobile remediation system capable of being pulled by a tractor and designed to operate as a sled, being pulled through contaminated spoil 11 and applying the analyzers 2, 3, 6 and adders 4, 5 sequentially in a remediation pathway, all under the direction of the controller 1.

Many changes and modifications can be made in the present invention without departing from the spirit thereof. We therefore pray that our rights to the present invention be limited only by the scope of the appended claims.

We claim:

1. A system for controlled verified remediation of contaminated spoil, comprising:
    a supply of sorbent capable of adsorbing contaminants;
    a supply of water;
    a remediation pathway conveying spoil from an intake point to an output point;
    a sorbent analyzer adapted to analyze characteristics and conditions of said supply of sorbent before use and to determine remediating potency of any specific supply of sorbent before adding the sorbent to the contaminated spoil;
    a pre-analyzer at said intake point adapted to analyze characteristics and conditions of contaminated spoil entering said remediation pathway;
    a water adder in said remediation pathway after said pre-analyzer, adapted to add water when necessary to increase moisture content of the contaminated spoil;
    a sorbent adder in said remediation pathway after said water adder, adapted to add a proper determined quantity of sorbent to said contaminated spoil;
    a post-analyzer at said output point adapted to analyze characteristics and conditions of remediated aggregate exiting said remediation pathway;
    a controller receiving data from and controlling operation of said sorbent analyzer, pre-analyzer, water adder, sorbent adder, and post-analyzer; and
    a set of remediation verification data derived and recorded by said controller;
    where said controller determines whether and how much water should be added by said water adder, and how much sorbent should be added by said sorbent adder, in accord with characteristics and conditions of said supply of sorbent and the contaminated spoil as analyzed by said sorbent analyzer and said pre-analyzer;
    where said controller verifies remediation of the contaminated spoil into aggregate in accord with characteristics and conditions of the remediated aggregate as analyzed by said post-analyzer; and
    where said controller derives, records, and reports said remediation verification data.

2. The system for controlled verified remediation of contaminated spoil of claim 1, further comprising a heat adder in said remediation pathway after said sorbent adder, adapted to apply heat to said supply of sorbent mixed with contaminated spoil.

3. The system for controlled verified remediation of contaminated spoil of claim 1, further comprising a remote controller in data communication with said controller, adapted to give personnel additional control and monitoring of said system.

4. The system for controlled verified remediation of contaminated spoil of claim 1, where said supply of sorbent is an adsorbent.

5. The system for controlled verified remediation of contaminated spoil of claim 1, where said supply of sorbent is a sorbent which combines with contaminants in a heat-producing reaction.

6. The system for controlled verified remediation of contaminated spoil of claim 1, where said supply of sorbent is a sorbent which reacts with contaminants in the presence of water.

7. The system for controlled verified remediation of contaminated spoil of claim 1, where said supply of sorbent is zeolite.

8. The system for controlled verified remediation of contaminated spoil of claim 1, where said supply of sorbent is silica gel.

9. A method for controlled verified remediation of contaminated spoil, comprising:
    providing a system for controlled verified remediation of contaminated spoil, comprising:

a supply of sorbent capable of adsorbing contaminants;
a supply of water;
a remediation pathway conveying spoil from an intake point to an output point;
a sorbent analyzer adapted to analyze characteristics and conditions of said supply of sorbent before use and to determine remediating potency of any specific supply of sorbent before adding the sorbent to the contaminated spoil;
a pre-analyzer at said intake point adapted to analyze characteristics and conditions of contaminated spoil entering said remediation pathway;
a water adder in said remediation pathway after said pre-analyzer, adapted to add water when necessary to increase moisture content of the contaminated spoil;
a sorbent adder in said remediation pathway after said water adder, adapted to add a proper determined quantity of sorbent to said contaminated spoil;
a post-analyzer at said output point adapted to analyze characteristics and conditions of remediated aggregate exiting said remediation pathway;
a controller receiving data from and controlling operation of said sorbent analyzer, pre-analyzer, water adder, sorbent adder, and post-analyzer; and
a set of remediation verification data derived and recorded by said controller;
where said controller determines whether and how much water should be added by said water adder, and how much sorbent should be added by said sorbent adder, in accord with characteristics and conditions of said supply of sorbent and the contaminated spoil as analyzed by said sorbent analyzer and said pre-analyzer;
where said controller verifies remediation of the contaminated spoil into aggregate in accord with characteristics and conditions of the remediated aggregate as analyzed by said post-analyzer; and
where said controller derives, records, and reports said remediation verification data;
operating said system for controlled verified remediation of contaminated spoil by feeding the contaminated spoil into said input end of said remediation pathway, removing the remediated aggregate from said output point of said remediation pathway, and generating a report of said remediation verification data.

10. The method for controlled verified remediation of contaminated spoil of claim 9, further comprising a heat adder in said remediation pathway after said sorbent adder, adapted to apply heat to said supply of sorbent mixed with contaminated spoil.

11. The method for controlled verified remediation of contaminated spoil of claim 9, further comprising a remote controller in data communication with said controller, adapted to give personnel additional control and monitoring of said system.

12. The method for controlled verified remediation of contaminated spoil of claim 9, where said supply of sorbent is an adsorbent.

13. The method for controlled verified remediation of contaminated spoil of claim 9, where said supply of sorbent is a sorbent which combines with contaminants in a heat-producing reaction.

14. The method for controlled verified remediation of contaminated spoil of claim 9, where said supply of sorbent is a sorbent which reacts with contaminants in the presence of water.

15. The method for controlled verified remediation of contaminated spoil of claim 9, where said supply of sorbent is zeolite.

16. The method for controlled verified remediation of contaminated spoil of claim 9, where said supply of sorbent is silica gel.

* * * * *